United States Patent
Loock et al.

(10) Patent No.: US 7,285,218 B2
(45) Date of Patent: Oct. 23, 2007

(54) METHOD FOR THE EXTRA-CORPOREAL QUALITATIVE AND/OR QUANTITATIVE RECORDING OF NEUROTOXIC SUBSTANCES IN THE BLOOD PLASMA OF AN INDIVIDUAL

(76) Inventors: Jan Loock, Drostenstrasse 22h, Rostock (DE) 18147; Steffen R. Mitzner, Thomes Mann Strass 7, Rostock (DE) 18055; Dieter G. Weiss, Blucherstrasse 63, Rostock (DE) 18055; Jan Stange, Buchenweg 4, Rostock (DE) 18059; Gunter W. Gross, 1312 Kendolph Dr., Denton, TX (US) 76205; Alexandra Gramowski, Foldstrasse 28, Rostock (DE) 18055; Dietmar Schiffmann, Lubecker Strasse 5, Rostock (DE) 18057

( * ) Notice: Subject to any disclaimer, the term of this patent is extended or adjusted under 35 U.S.C. 154(b) by 346 days.

(21) Appl. No.: 10/476,440

(22) PCT Filed: May 3, 2002

(86) PCT No.: PCT/DE02/01609

§ 371 (c)(1),
(2), (4) Date: Jun. 7, 2004

(87) PCT Pub. No.: WO03/001201

PCT Pub. Date: Jan. 3, 2003

(65) Prior Publication Data
US 2004/0211727 A1 Oct. 28, 2004

(30) Foreign Application Priority Data
Jun. 22, 2001 (DE) ................................ 101 29 693

(51) Int. Cl.
*B01D 11/00* (2006.01)
*C12N 13/00* (2006.01)
*G01V 3/00* (2006.01)
*B01D 61/00* (2006.01)

(52) U.S. Cl. ....................... 210/634; 210/645; 436/811; 436/820; 436/825; 435/173.1; 435/69.1; 324/347

(58) Field of Classification Search ................ 210/645, 210/634; 607/2; 600/300; 604/48; 536/23.5; 435/69.1, 325, 335, 9.2, 173.1; 324/347; 436/811, 820, 825
See application file for complete search history.

(56) References Cited

U.S. PATENT DOCUMENTS

| 5,480,554 | A | 1/1996 | Degen et al. |
| 6,911,474 | B2 * | 6/2005 | Piomelli et al. ............ 514/563 |
| 7,033,500 | B2 * | 4/2006 | Bomberger et al. ..... 210/321.79 |
| 7,064,147 | B2 * | 6/2006 | Barta et al. ................. 514/561 |

FOREIGN PATENT DOCUMENTS

| DE | 4315718 | 11/1993 |
| DE | 19544297 | 6/1997 |
| DE | 19932720 | 1/2001 |
| EP | 0760103 | 3/1997 |

OTHER PUBLICATIONS

Reaction of the Neuronal Networks in Vitro to Ulrafiltrates of Liver Coma Plasma Influence of Mars Treatments, J. Loock, J. Stange, S. Mitzner, R. Schmidt, D. Schiffman, D. Weiss, E.W. Keefer, G.W. Gross; Artif Organs, vol. 23, No. 7, 1999.

Reaction of the Neuronal Networks in Vitro to Ultrafiltrates of Liver Coma Plasma Influence of Mars Treatments, J. Loock, J. Stange, S. Mitzner, R. Schmidt, D. Schiffman, D. Weiss, E.W. Keefer, G.W. Gross; The International Journal of Artificial Organs, vol. 22, No. 6, 1999.

* cited by examiner

*Primary Examiner*—Ana Fortuna
(74) *Attorney, Agent, or Firm*—Michael L. Dunn

(57) ABSTRACT

The invention relates to a method for the extra-corporeal qualitative and/or quantitative recording of neuro-toxic substances in the blood plasma of an individual. According to Arrangement of the cell assembly on a two-dimensional carrier with integrated microelectrodes for deriving the electrical signals and microconductors said method, a system containing neurones or neuronal networks, which have been cultivated on or applied to a micro-electrode array or a neuro-chip, in addition to a device for measuring the electrical activity of at least one or several of said neurones are provided, the neurones are brought into contact with a prepared sample of plasma and the electrical activity of the neurones is measured. The aim of the invention is to develop and improve said method in such a way that it supplies reliable, reproducible results for the recording of neuro-toxic substances in the blood plasma of an individual, in particular in the case of encephalopathic conditions, such as for example hepatic failure, or of coma conditions of various origins. To achieve this, prior to measurement, the blood plasma of an individual is prepared by being subjected to a filtration method, preferably an ultra-filtration method, whereby an exclusion limit, which causes the most extensive separation possible of the plasma protein from the other dissolved substances is selected, and/or prior to measurement, the blood plasma of an individual is prepared by being subjected to an extraction of liposoluble substances, using a solvent for liposoluble substances, and the ultra-filtrate or the extract containing the liposoluble substances, or both are used in succession or are blended together for the measurement.

18 Claims, 5 Drawing Sheets

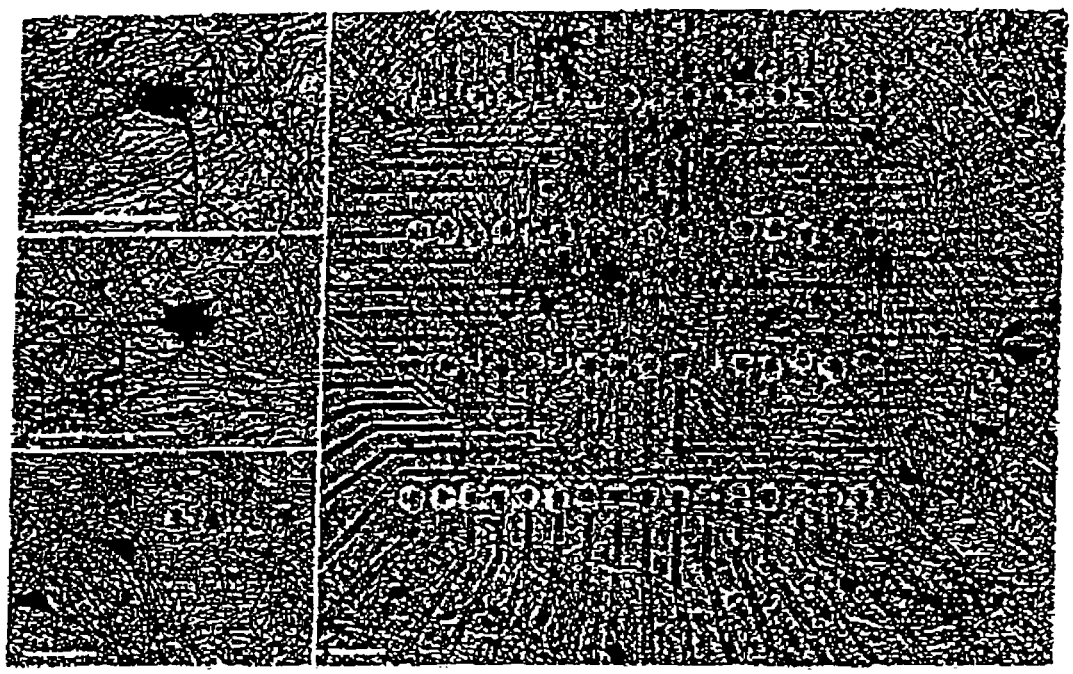
Fig 1: Arrangement of the cell assembly on a two-dimensional carrier with integrated microelectrodes for deriving the electrical signals and microconductors

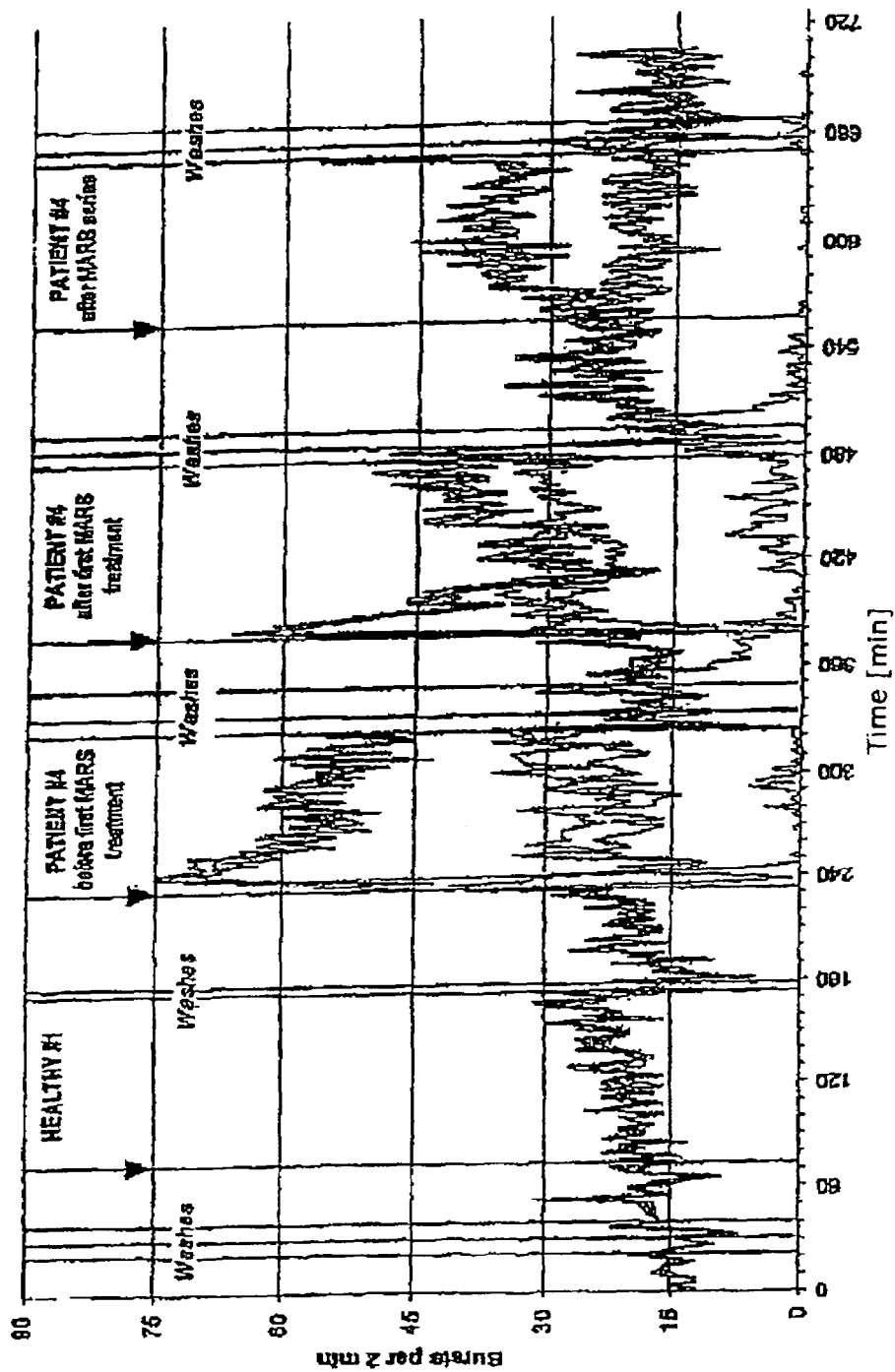
Fig 2a: Change in the electrical activity of the neuronal network upon the addition of ultrafiltrates of a healthy experimentee (HEALTHY #1) and a patient (PATIENT #4) with severe liver failure with hepatic encephalopathy of high degree prior to and during ongoing therapy, entailing a marked reduction in the degree of coma

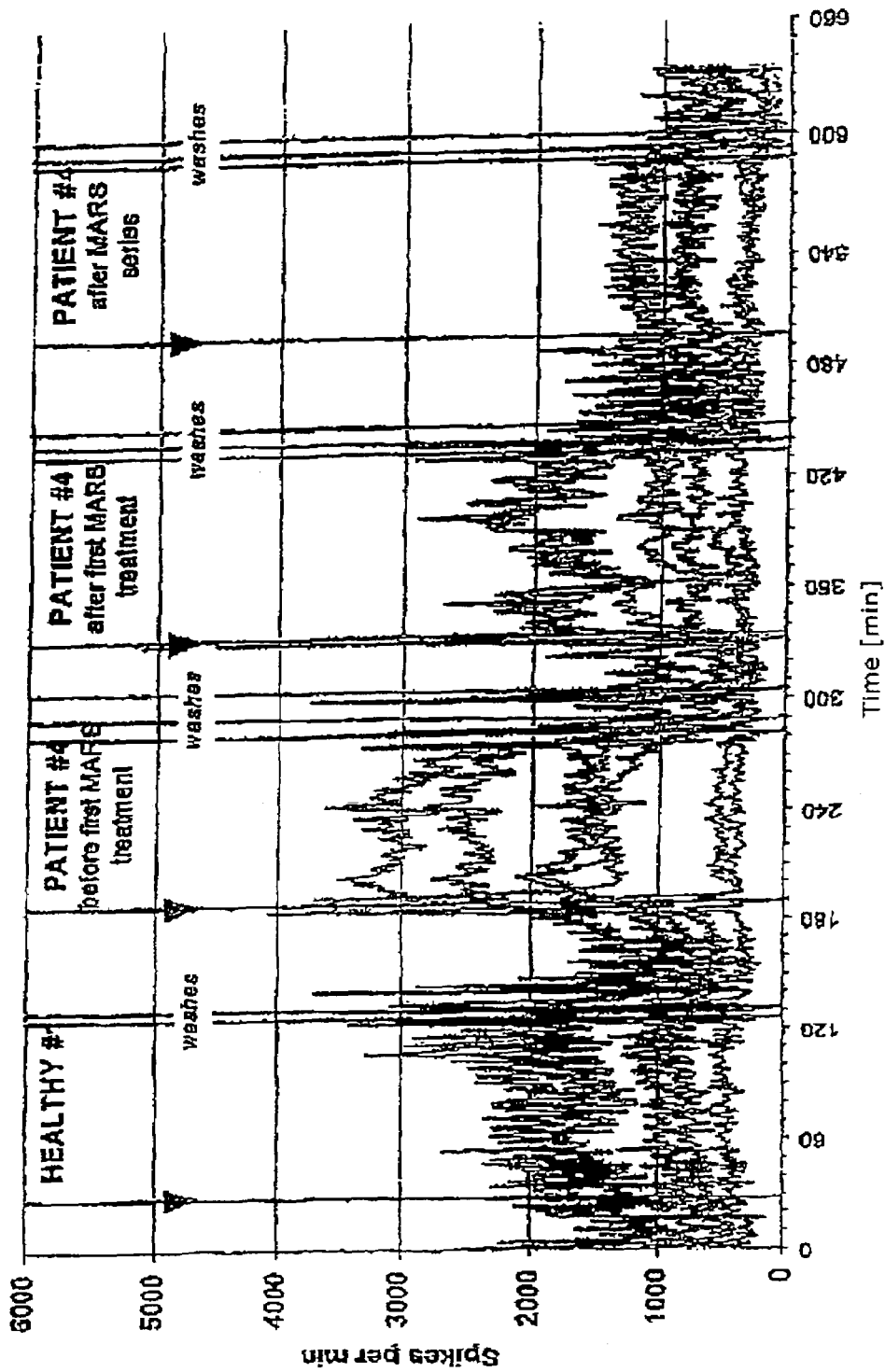
Fig 2b: Change in the electrical activity of the neuronal network upon the addition of ultrafiltrates of a healthy experimentee (HEALTHY #1) and a patient (PATIENT #4) with severe liver failure with hepatic encephalopathy of high degree prior to and during ongoing therapy, entailing a marked reduction in the degree of coma

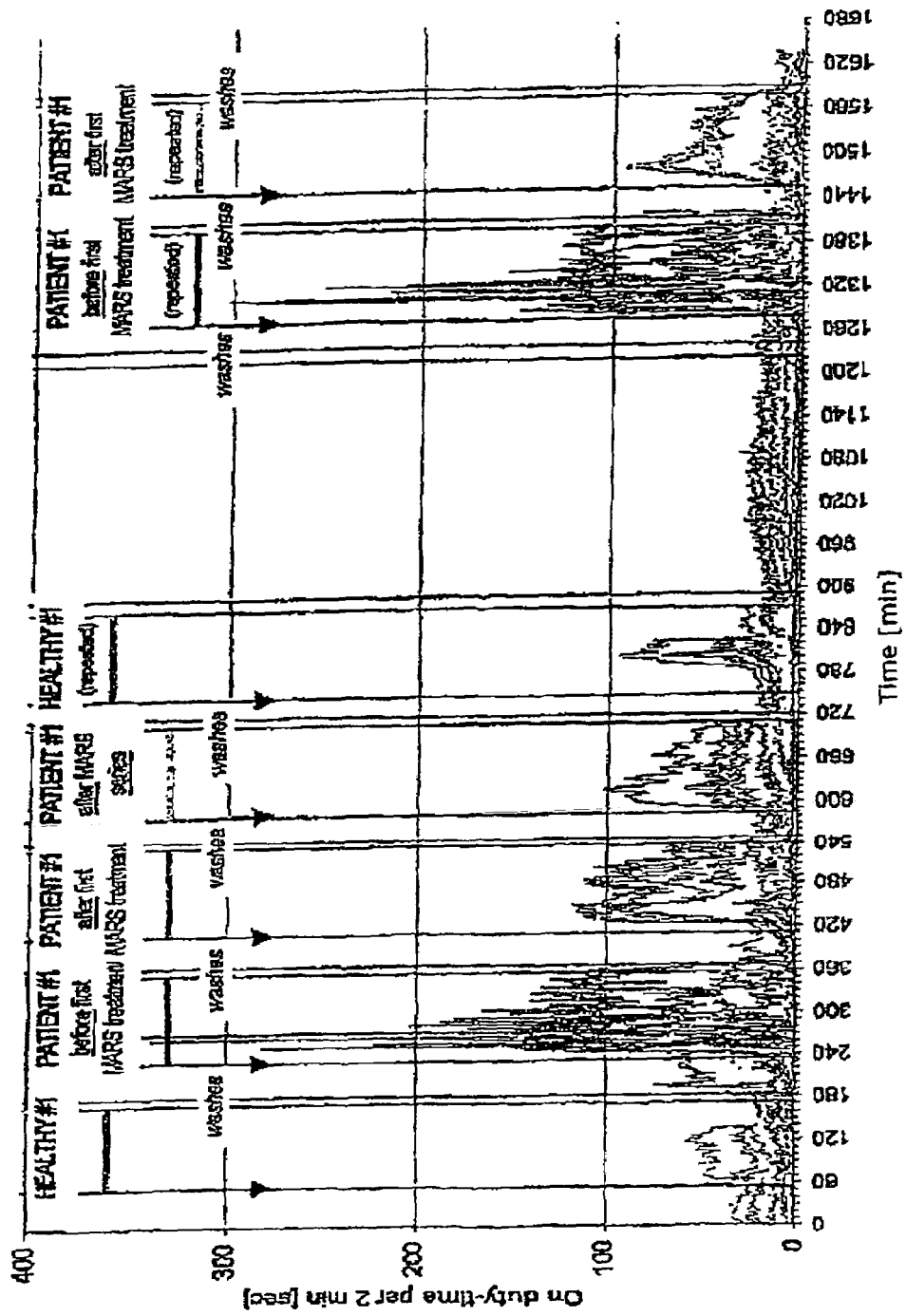
Fig 3: Change in the electrical activity of the neuronal network on the basis of the addition of ultrafiltrates of a healthy experimentee (HEALTHY #1) and another patient in Figures 2a and 2b (PATIENT #1) with severe liver failure with hepatic encephalopathy of high degree prior to and during ongoing therapy, entailing a marked reduction in the degree of coma

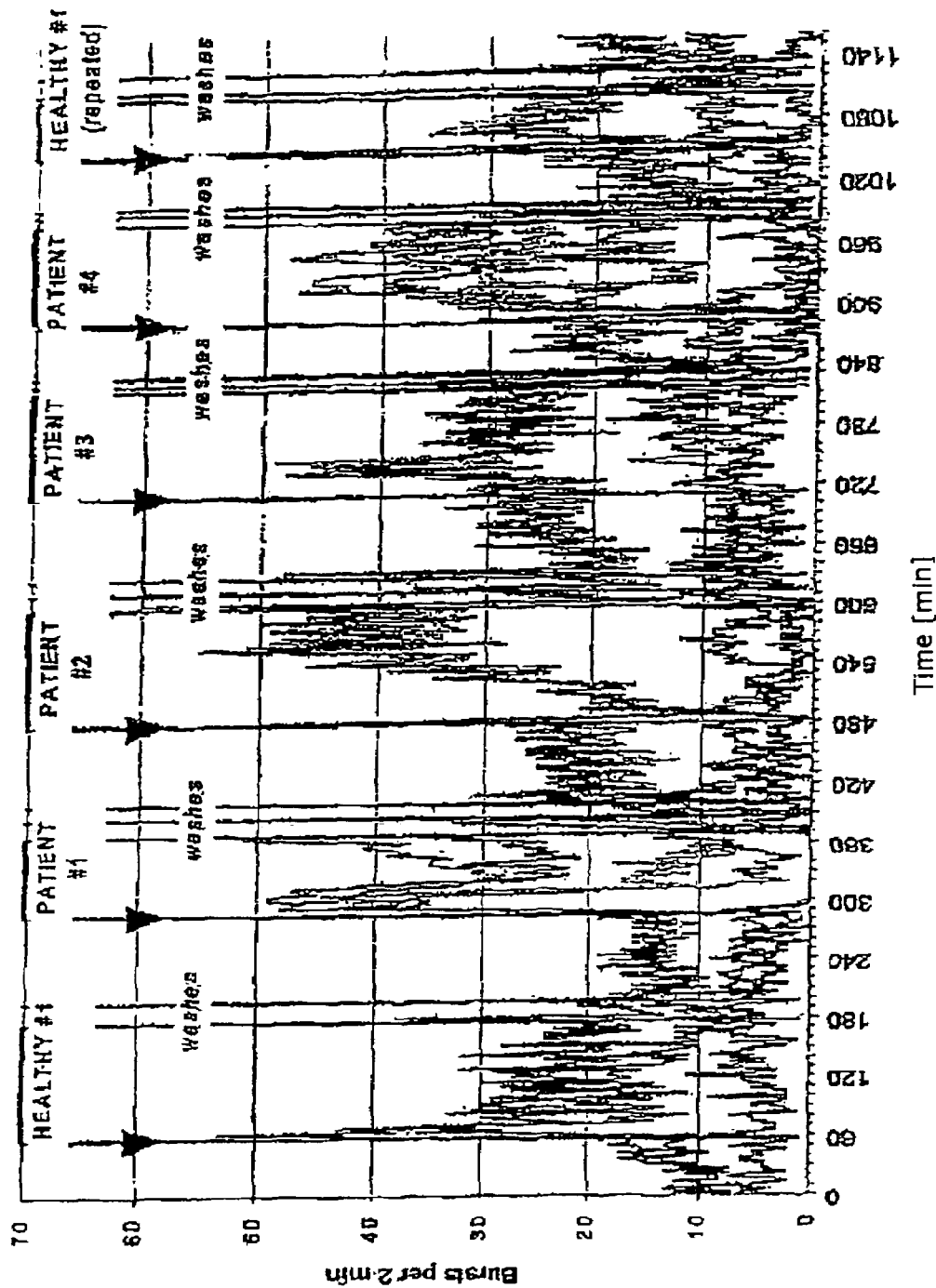
Fig 4: Change in the electrical activity of the neuronal network upon the addition of ultrafiltrates of a healthy experimentee (HEALTHY #1) and four different patients (PATIENT #1 - #4) with liver failure and with hepatic encephalopathy of high degree without previous dialysis treatment.

METHOD FOR THE EXTRA-CORPOREAL QUALITATIVE AND/OR QUANTITATIVE RECORDING OF NEUROTOXIC SUBSTANCES IN THE BLOOD PLASMA OF AN INDIVIDUAL

The invention concerns a method of extracorporal qualitative and/or quantitative detection of neurotoxic substances in the blood plasma of an individual, in which there is provided a system with neurons or neuronal networks applied or cultivated on a microelectrode array or a neurochip and a device for measuring the electrical activity of at least one or more of the neurons, the neurons are brought into contact with a processed plasma sample and the electrical activity of the neurons is measured.

STATE OF THE ART

A large number of disease conditions in medicine can involve a reduction in consciousness of the patient, down to the state of a coma. Often that reduction is attributed to a change in the composition of the blood plasma (metabolic encephalopathies, for example in the context of liver or kidney failure, diabetic coma, poison conditions, or the effect of medication).

Among the metabolic encephalopathies which are caused by the extensive failure of important detoxification systems of the body such as liver or kidneys, hepatic encephalopathy, by virtue of the frequency of the occurrence of severe liver diseases and hitherto still inadequate therapeutic options, is of major medical and socio-economic relevance. The precise mechanisms involved in the occurrence thereof in contrast are still substantially unexplained. In accordance with the present state of knowledge it is assumed that the cause is an influence in respect of the central-nervous function by metabolites accumulating in the liver failure, caused by losses of function of organs which are important in terms of discharge or detoxification of metabolic end products, such as the liver or kidneys. In the course of time the situation involves a progredient encephalopathy which in clinical terms makes an impression by virtue of undulating alterations in the degree of alertness, attentiveness and capacity for concentration as well as extrapyramidal motor disturbances such as increased muscle tone and tremor. Added to that are confusion, misperceptions and hallucinations. In severe cases this leads to delirium, coma and finally the death of the patient. In regard to the mechanisms which lead to functional reductions in the central nervous system, various hypotheses exist. They include the theory of the false neurotransmitters (Fischer, J. E., Baldessarini, R. J.: False neurotransmitters and hepatic failure. Lancet 2, (1975), 75-80), the ammonia hypothesis (Blei, A. T., Olafsson, S., Therrien, G., Butterworth, R. F.: Ammonia-induced brain edema and intracranial hypertension in rats after portocaval anastomosis. Hepatology 19, (1994), 1437-1444; Butterworth, R. F.: Pathophysiology of hepatic encephalopathy: the ammonia hypothesis revisited. In: Progress in hepatic encephalopathy and metabolic nitrogen exchange. Publishers: Bengtsson, F., Boca Raton, CRC Press, 1991, 9-24), the GABA-benzodiazepine receptor ligand hypothesis (Basile, A. S., Harrison, P. M., Hughes, R. D., Gu, Z. Q., Pannell, L., McKinney, A., Jones, E. A., Williams, R.: Relationship between plasma benzodiazepine receptor ligand concentrations and severity of hepatic encephalopathy. Hepatology 19, (1994), 112-121) and the synergism theory about the mutually reinforcing actions of a plurality of responsible metabolites (Zieve L.: Role of toxins and synergism in hepatic encephalopathy. In: Hepatic encephalopathy. Publishers Butterworth, R. F., Humana Press, Clifton, N.J., 1989, 141-156). The hitherto identified potential toxins involve ammonia, bilirubin, gallenic acids, tryptophan, phenolic and indolic decomposition products of amino acids, mercaptans, medium-chain fatty acids and endogenous benzodiazepines (Weissenborn, K.: Recent developments in the pathophysiology and treatment of hepatic encephalopathy. Ballière's Clin. Gastroenterol. 6, (1992), 609-630). What is common to those theories is that the substances accumulated in the body as a consequence of the organ failure involve a central part in the pathogenesis of the encephalopathy caused (Jones, E. A. Gammal, S. H.: Hepatic encephalopathy. In: The liver. Biology and Pathobiology, second edition, Publishers: Arias, I. M., Raven Press, Ltd., New York, 1988, 985-1004; Record, C. O.: Neurochemistry of hepatic encephalopathy. Gut 32, (1991), 1261-1263). The cause of the lack of clarity, which still persists, about the pathophysiological processes which take place in the brain is in particular the difficulties involved in affording definitive proof on in vivo models. Even the precise mechanisms involved in the occurrence of many other coma conditions are still substantially unexplained. Often the measurement of individual laboratory parameters which in accordance with the present state of knowledge are deemed to be pathogenetically significant does not correlate with the clinically existing degree of loss of consciousness. A comparison of the effects of plasma samples of patients with the effects of various pure substances can contribute to the identification of possible triggers of the coma and thus elucidating the pathogenesis of those forms of disease.

Particularly in relation to coma conditions of an unclear nature, which may involve poisoning situations or suicide attempts, in the context of emergency medicine when there is a vital threat to the patient there is frequently the need for detection and quantification as immediately as possible of the triggering poison or toxic substance, in order to initiate a form of treatment which is organized in the optimum fashion.

A new kind of dialysis procedure for extracorporal detoxification is used, under the name MARS (Molecular Adsorbents Re-circulating System, Teraklin AG, Rostock), which was developed specifically for eliminating toxic compounds from the plasma of patients in liver failures (Stange, J., Mitzner, S., Ramlow, W., Gliesche H., Hickstein, H., Schmidt, R.: A new procedure for the removal of protein-bound drugs and toxins. ASAIO J. 39, (1993), M621-M625). Besides water-soluble metabolites this also involves relatively lipophilic substances. The latter are transported in the blood bound primarily to plasma proteins—in particular albumin. By virtue of the presence of acceptor proteins (albumin) in the dialysate MARS permits the elimination of those otherwise scarcely dialyzable compounds from the blood plasma (Stange, J., Ramlow, W., Mitzner, S., Schmidt, R., Klinkmann, H.: Dialysis against a recycled albumin solution enables the removal of albumin-bound toxins. Artif. Org. 17, (1993), 809-813; Stange, J., Mitzner, S. R., Risler, T., Erley, C. M., Lauchart, W., Göhl, H., Klammt, S., Peszynski, P., Freytag, J., Hickstein, H., Löhr, M., Liebe, S., Schareck, W., Hopt, U. T., Schmidt, R.: Molecular Adsorbents Recirculating System (MARS): Clinical results of a new membrane-based blood purification system for bioartificial liver support. Artif. Org. 23, (1999), 319-330). In addition, that also achieves a favorable influence in respect of the amino acid dysbalance, which is otherwise typical in that syndrome, between branched-chain and aromatic amino acids in the plasma (Loock J., Peters E, Stange J, Mitzner S, Perszynski P, Klammt S, Liebich H, Schmidt R: Change of human serum albumin amino acid patterns (Fischer-Index) during a new dialysis treatment for liver failure (MARS). Internat J Artif Org 20 (1997) 500). In the context of clinical use of that procedure on patients in a liver coma in studies it was found that there was a significant reduction in the degree of encephalopathy of the patients (Stange J, Mitzner S, Klammt S, Freytag J, Peszynski P, Loock J, Hickstein H, Korten G, Schmidt R, Hentschel J, Schulz M, Löhr M, Liebe S, Schareck W, Hopt UT: Liver Support by Extracorporal Blood Purification-A Clinical Observation. Liver Transpl. 2000 September; 6(5); 603-13).

The clinical assessment of the degree of hepatic encephalopathy attributed to liver failure is however made difficult or entirely impossible under some circumstances due to the presence of other coma-triggering factors or effects of drugs. Hitherto there has not been a method of quickly and reliably monitoring the success of a treatment, that is to say the degree of detoxification during and after the treatment.

In consideration of the multi-morbidity which is often present in respect of those high-risk patients disturbances in the function of the central-nervous system can also be due to other diseases which are additionally present. In this context, arriving at the correct diagnosis is often possible only with a delay. Specific examples in regard to other kinds of triggers of cerebral functional disturbances in this context can be infections (for example meningitis, abscesses, encephalitis) or side-effects of drugs but also circulatory disturbances in the brain or the accumulation of kidney-related metabolites in the context of a complicating kidney failure. An improved diagnosis which permits detection in good time of another cause leading to the effect on consciousness would improve the prognosis of the patients, by virtue of early initiation of the appropriate therapy, and would reduce the duration of a stay in highly cost-intensive intensive care units.

The development of neuronal networks on microelectrode arrays permits the continuous recording and analysis of the electrical activity of neuron assemblies under different experimental conditions (Gross, G. W., Rieske, E., Kreutzberg, G. W., Meyer, A.: A new fixed-array multimicroelectrode system designed for longterm monitoring of extracellular single unit neuronal network activity in vitro. Neurosci. Lett. 6. (1977), 101-105; Gross, G. W.: Internal dynamics of randomized mammalian neuronal networks in culture. In: Enabling technologies for cultured neural networks. Publishers: Stenger, McKenna, T. M., Academic Press, New York, 1994, 277-317). Previous works show that the network activity is influenced by the application of a multiplicity of neuronally active substances in each case in concentration-specific and substance-specific and generally reversible fashion. Only cell-toxic concentrations irreversibly terminate network activity (Gross, G. W.: Internal dynamics of randomized mammalian neuronal networks in culture. In: Enabling technologies for cultured neural networks. Publishers: Stenger, McKenna, T. M., Academic Press, New York, 1994, 277-317). That affords completely novel possible options in terms of qualitative and quantitative detection of the pathophysiological processes in the brain.

DE 19932720 A1 describes a method of measuring the action of substances such as pharmacological substances and toxins on a neuronal cell assembly. The method provides that neurons are applied in solution to a multielectrode array (neurochip), the bioelectric activity of the cell assembly is measured and a defined activity state is set by varying at least one ion concentration in the extracellular solution. Then, the substance to be investigated is added to the extracellular solution and the activity of the cell assembly or the change therein is measured again. The method is intended to permit screening of substances in respect of their effectiveness on neuronal excitability, synaptic transfer and/or network behavior. As the activity states are based on the interaction of cellular and synaptic mechanisms, the cell assemblies have a very sensitive reaction to the effect of extracellularly added substances. It is possible in that way to very well and in particular reproducibly test the action of the substance or material to be tested. In addition knowledge of the dependencies of the network states on extracellularly manipulatable parameters (neuronal excitability and effectiveness of synaptic transfer) permits good calibration and thus makes it possible to set a defined test state. DE 19932720 A1 relates essentially to the production and calibration of the system. The only test substance used was a 100 μM solution of 4-aminopyridine.

It was found however that the method in accordance with DE 19932720 A1 of detecting neurotoxic substances in the blood plasma or serum of patients cannot be readily used in a reproducible fashion. In contrast to pure substances as were used as a test substance in DE 19932720 A1 blood plasma contains a mixture of a large number of proteins and other lipophilic and hydrophilic substances. The proteins can act as carriers for different substances with only a low level of water solubility and thus permit the transport thereof in the blood circulation. Other proteins however involve functions in the non-specific and specific (immunological) defense of substances which are recognized in the organism as being foreign and microorganisms (complement factors, immunoglobulins). As the neuronal networks are obtained from fetuses of mammals (for example a mouse), upon the addition of blood plasma or serum to the sensor system, the procedure involves contact of the plasma proteins with the cells of a foreign species. That can cause activation of the complement system and specific immunological interactions, as a consequence of which the cells recognized as foreign are attacked and damaged by the defense system. In addition the other lipophilic and hydrophilic substances are in part present in the plasma of encephalopathic or comatose patients, for example in a liver failure situation, in different levels of concentration, that is to say higher or lower, or in different configurations, binding or charge conditions, from in the plasma of healthy people. They therefore represent potential indicators for a given disease condition. On the other hand however a plurality of substances is also present in the plasma, which are not specific indicators in respect of the particular syndrome and/or considerably influence or disturb the electrical activity of the neurons in the known test method and thus also the results obtained in measurement of the currents, and make it very difficult to obtain reliable reproducible information about the measurement results.

Therefore the object of the present invention is to develop and improve the per se known method of detecting neurotoxic substances by means of a neuronal network in a culture on a microelectrode array, in such a way that it produces reliable and reproducible results for the detection of neurotoxic substances in the blood plasma of an individual, particularly when encephalopathic conditions apply such as in a liver failure situation or when there are coma states of a different cause.

That object in accordance with the invention is attained by a method of the kind set forth in the opening part of this specification, which is characterized in that the blood plasma of the individual is subjected to a filtration process, preferably an ultrafiltration operation, for preparation prior to the measurement operation, wherein an exclusion limit is selected for the molecular weight, which provides for very substantial separation of the plasma proteins from the other dissolved substances, and/or the plasma of the individual is subjected to an operation for the extraction of fat-soluble substances using a solvent for fat-solvent substances, for preparation prior to the measurement operation, and the ultrafiltrate or the extract containing fat-soluble substances or both in succession or as a mixture are used for the measurement operation.

It was possible to show (see below) that blood plasma samples prepared in a given manner from healthy individuals and comatose patients, for example in a liver failure situation, caused reproducibly different electrical excitation states in neuronal networks on a microelectrode array (neurochip), more specifically in such a fashion that the samples originating from healthy individuals respectively caused no or only slightly pronounced variations in comparison with the initial activity of the neuronal network while the samples from comatose patients in a liver failure situation respectively caused a great change in that activity. When using blood plasma which was not pre-treated in accordance with the method of the invention the activity of the cell assembly was already greatly influenced upon the addition of samples of healthy individuals so that the differences in relation to comatose patients were considerably less pronounced or not recognizable at all. That was attributed to the fact that given substances which are present both in the blood of healthy patients and also ill patients greatly influence the electrical activity of the neurons in the same manner so that reactions on the part of the neurons to disease-specific substances were superimposed as a result. Interactions between the above-mentioned proteins contained in the plasma and serum for defending against foreign substances and pathogens with the surfaces of the cell assembly very probably have a great significance in terms of triggering those effects. Therefore, a significant distinction between plasma of healthy individuals and comatose patients was not possible or was not possible with sufficient clarity for reproducible use of the method.

Specific changes in the neuronal activity after the addition of a prepared plasma or serum sample from the patient can give important indications in regard to the underlying cause of the coma and permit specifically targeted further diagnosis and therapy. Quantitative detection of the change in neuronal activity after sample addition not only provides for information about the degree of the intoxication present but upon investigation of a plurality of samples of a patient in the course of the disease also permits an assessment of the effectiveness of the form of therapy applied.

Surprisingly it was found that, with blood plasma which prior to the measurement operation had been subjected to ultrafiltration with an exclusion limit for the molecular weight of 60,000 Daltons, that afforded a neuron excitation which is to be more markedly distinguished, between plasma from healthy individuals and ill patients. The results were still more clearly marked with an exclusion limit for the molecular weight of 45,000 Daltons and even better 30,000 Daltons.

The excitation currents measured for example with blood plasma from patients with liver failure were significantly higher than those which were measured with blood plasma from healthy individuals, subjected to ultrafiltration in the same manner. It was also possible to show that the strength of the neuron excitation effects correlated with the severity of the symptoms. In the case of plasma samples from patients whose blood was subjected to liver dialysis, for example using the MARS process, a continuous reduction in the level of excitation in the course of dialysis was observed. It was thus possible to establish a reproducible correlation between the concentration of disease-specific substances in the blood plasma and the level of the excitation currents. It was further found that the variation in the excitation currents during a measurement operation when dealing with plasma samples from various patients with the same symptoms was very similar over the time of the measurement operation, that is to say it exhibited a comparable excitation pattern. On the basis of the excitation pattern which was measured from a blood plasma sample from a patient, which was subjected to ultrafiltration in accordance with the method of the invention, it was thus possible to produce a qualitative and quantitative relation by comparison with standards from healthy patients and standards from patients with known symptoms and a known severity of illness.

The high-molecular substances which can be separated by ultrafiltration from blood plasma primarily involve higher-molecule proteins such as for example antibodies, albumin and so forth. When separating off those proteins by ultrafiltration, relatively good water-soluble compounds are obtained for the major part in the ultrafiltrate, while fat-soluble substances were contained only to a slight degree. That is attributed to the fact that some of the fat-soluble substances bind to the high-molecular proteins and as a result are also separated from the plasma in the ultrafiltration operation. It was however also possible to show that the fat-soluble substances in the blood plasma produce their own effects on the activity of the neuronal networks in the method of the present invention, which in turn were caused only by samples from comatose patients.

In accordance with the invention therefore an extract of the fat-soluble substances from the blood plasma can also be used alone or in combination with the ultrafiltered plasma samples used in accordance with the invention. For that purpose the blood plasma is mixed with a preferably organic solvent and extracted. In a preferred embodiment of the invention dichloromethane or chloroform is used for that purpose. After good thorough mixing of the blood plasma with the organic solvent, the mixture is left to settle and the phases are separated.

The organic phase with the fat-soluble substances dissolved therein is removed, the solvent can be evaporated and the residue, with the fat-soluble substances, is again dissolved or suspended, preferably in the same or a similar medium, in which the cultivated neuronal networks are disposed on the microelectrode array. Preferably a mixture of cell culture medium and a low level of concentration of a dissolving intermediary such as dimethyl sulfoxide, is used for the re-suspension procedure.

In a particularly preferred embodiment of the invention the blood plasma is acidified prior to the extraction operation with the organic solvent. Preferably an inorganic acid such as hydrochloric acid is used for that purpose. Due to the acidification operation, acid organic substances such as organic acids which are present under the pH-value conditions of the blood plasma in an equilibrium between the protonized and the deprotonized condition are more greatly protonized and thus the equilibrium is shifted to the favor of a protonized and more fat-soluble condition. That provides that more of such acid substances can be transferred from the plasma into the extract.

The combined measurement of ultracentrifuged and extracted plasma samples, whether in succession or as a mixture is particularly preferred in accordance with the invention. The determination procedure on the basis of two different preparations of one and the same plasma sample which generally results in qualitatively and/or quantitatively different excitation patterns affords the possibility of comparing a larger number of standards both for blood from healthy patients and also blood from patients with different syndromes and severities of disease with the blood samples to be investigated, thereby considerably improving the reliability of the results and the reproducibility factor.

In the context of the work relating to this invention essentially the effect of plasma samples from patients with metabolic encephalopathies on the electrical activity of neuronal networks was investigated in vitro. The results showed that ultrafiltrates and extracts of such samples, in comparison with samples from healthy patients, produce a marked change in the network activity. That correlated with the degree of the existing encephalopathy of the patient. Investigations on the basis of a large number of neuronally active substances demonstrated the dose and substance specificity of the network reactions and the very good reproducibility of the results obtained on the same and on different networks. The system of the neurons or neuronal networks cultivated on microelectrode arrays can thus be advantageously used for diagnosis and differential diagnosis of metabolic encephalopathies and for monitoring existing and new therapy concepts.

The application of the method according to the invention, as a consequence, permits improved, specifically targeted treatment of patients, which in turn results in a reduction in morbidity and mortality. In addition, early initiation of an appropriate therapy makes it possible to achieve a saving in cost by virtue of the patients spending shorter periods of time in the intensive care area and in the hospital. Identification of the pathomechanisms underlying the encephalopathies, by means of the method according to the invention, could also afford approaches for the development of novel preventative and therapeutic strategies.

EXAMPLES

Ultrafiltration

The ultrafiltration of the plasma samples was implemented with ultrafilters from Schleicher & Schüll, Germany, for sample volumes in each case of 0.5 ml, with an exclusion size in respect of the membrane of 30,000 Daltons, according to the manufacturer's specification.

Extraction

500 µl of a plasma sample to be investigated was acidified in a 2 ml Safe-Lock reaction vessel (Eppendorf, Hamburg) with 150 µl of hydrochloric acid (37%, for analysis, Merck, Darmstadt). After the addition of 1,000 µl of dichloromethane (for analysis, Merck, Darmstadt), the sample is intensively mixed using a mixer (Gyrator Uniprep, UniEquip, Martinsried) for 3 minutes and then centrifuged for 5 minutes at 20800×g (Centrifuge 5417 C, Eppendorf, Hamburg). The lower organic phase (dichloromethane phase) was removed, transferred into a new 2 ml Safe-Lock reaction vessel and carefully evaporated at ambient temperature. After complete evaporation of the solvent the deposit remaining in the vessel was dissolved again in 500 µl of a 1% dimethyl sulfoxide-(DMSO)-solution in DMEM (Dulbecco's Minimal Essential Medium). Mixing of the sample was effected by renewed shaking in the above-described manner. The plasma sample prepared in that way was brought into contact with the neurons for the measurement operation.

Production of Neuronal Networks on Microelectrode Arrays—Fetal Mouse Brain Culture/Fetal Rat Brain Culture The cultivation of neurons on microelectrode arrays (neurochips) was implemented in accordance with known procedures (Gross, G. W., Internal Dynamics of randomized mammalian neuronal networks in culture. In: Enabling Technologies for Cultured Neuronal Networks (Stenger, D. A. and McKenna, T. M., eds.), Academic Press, New York, 1994, pages 277-317; DE 199 32 720 A1 to Siebler et al.).

Preparation of the sensor cell culture surface for the growth with nerve cell cultures includes sterilization (for example with alcohol, UV-light, gamma rays), hydrophilization of the surface (for example a flaming-off step, acid or lye treatment with subsequent washing) and the application of cationic charge carriers and/or adhesion factors (individually, in combination or as a mixture), for example polylysin, polyethylene imine, laminin and fibronectin).

The brains or parts thereof are prepared from fetuses (day 15-18 of pregnancy). The cell assembly is mechanically reduced in size in a buffer solution, with scalpel blades. Then constituents of the extracellular matrix and cell membrane proteins are subjected to initial digestion by adding digestion enzymes. The action of the digestion solution is stopped by the addition of protein-bearing nutrient solution and the tissue is put into nutrient medium after the blocked digestion solution is sucked away. The cells are separated by careful up-and-down pipetting.

Then, depending on the kind of animal and the tissue of origin, the cell suspension is sown in a density of 50,000 to 1 million cells/cm$^2$ on the pretreated sensor-cell culture surface of the neurochips. The neurochips are put into plastic bowls with a cover and put into an incubation cabinet (37° C., air with 5-10% carbon dioxide addition, 90-95% air humidity). A part of the consumed nutrient medium is replaced by fresh medium twice to three times weekly.

The cells (a mixture of nerve cells and glia cells which have supporting and metabolic functions) adhere to the sensor-cell culture surface and extensions grow from the nerve cells and form links with each other. In that situation there is close contact with the glia cells so that the result is a nerve network which is similar in composition to the original tissue. It develops in the course of some days to weeks a spontaneous electrical activity pattern which is tissue-typical and which can be measured by coupling the cells to the sensors.

EMBODIMENT

Dissociated fore-brain cortex tissue from 18 day-old mouse embryos was cultivated on microelectrode array plates with 64 thin film electrodes on an area of 1 mm$^2$. The cells were kept in culture in accordance with the above-specified process described by Gross. Plasma samples were taken from two healthy experimentees (male) and four patients suffering from liver failure, who were subjected to liver dialysis with the MARS system (see Table 1). Higher-molecular proteins were removed by means of ultrafiltration in accordance with the above-described method with an exclusion size of 30,000 Daltons.

TABLE 1

Patient characteristics and degree of hepatic encephalopathy (HE)

| Number | Sex/Age | Syndrome | Degree of HE |
|--------|---------|----------|--------------|
| 1 | female/24 years | Decompensated alcoholic liver cirrhosis | Degree III |

TABLE 1-continued

Patient characteristics and degree of hepatic encephalopathy (HE)

| Number | Sex/Age | Syndrome | Degree of HE |
| --- | --- | --- | --- |
| 2 | female/43 years | Alcoholic liver cirrhosis, hepatorenal syndrome | Degree II-III |
| 3 | female/46 years | Alcoholic liver cirrhosis, hepatorenal syndrome | Degree II-III |
| 4 | male/44 years | Decompensated alcoholic liver cirrhosis | Degree III |

The experiments were carried out in an open high-quality steel chamber which was covered with a removable heated plastic cover and in which a temperature of 37° C. obtained, in an atmosphere consisting of air with 10% $CO_2$. The cells were regularly checked by light microscope means. For improved documentation of the morphological changes in the cells during the experiment a time-dependent recording was implemented in parallel. The electrical activity of the electrodes was amplified and digitally detected (software from Spectrum Scientific, Dallas, Tex., USA). After the experiment was set up the cultures were left to stand for between 30 minutes and 1 hour so that their background activity could be established. Thereafter the spontaneous activity of the neuronal networks was recorded for at least 30 minutes. Equal proportions of 100 microliters of the ultrafiltrates of the human blood plasma in each case were then added to 600 microliters of culture medium on the neuronal network and left to stand for up to 2 hours. The culture was then washed at least twice with cell culture medium and the activity of the neuronal networks recorded again for at least 30 minutes before the next sample to be investigated was added.

DESCRIPTION OF THE FIGURES

FIG. 1 shows a diagrammatic view of the arrangement of the cell assembly on a two-dimensional carrier with integrated microelectrodes for deriving the electrical signals and microconductors, FIGS. 2a and 2b show the change in electrical activity of the neuronal network upon the addition of ultrafiltrates of a healthy experimentee (HEALTHY #1) and a patient (PATIENT #4) with severe liver failure with hepatic encephalopathy of high degree prior to and during ongoing therapy, entailing a marked reduction in the degree of coma, FIG. 3 shows the reproducibility of the change in electrical activity of the neuronal network as is shown in FIGS. 2a and 2b on the basis of the addition of ultrafiltrates from a healthy experimentee (HEALTHY #1) and another patient (PATIENT #1) with severe liver failure with hepatic encephalopathy of high degree prior to and during ongoing therapy, entailing a marked reduction in the degree of coma, and FIG. 4 shows a comparison of the change which occurs in electrical activity of the neuronal network upon the addition of ultrafiltrates of a healthy experimentee (HEALTHY #1) and four different patients (PATIENT #1-#4) with liver failure with and with hepatic encephalopathy of high degree without previous dialysis treatment.

FIG. 1 shows the arrangement of an neuronal cell assembly between glia cells and other cellular elements naturally present in the central nervous system (fibroblasts, endothelium cells) on a multielectrode array, wherein the neuronal cells are linked to each other by synaptic connections and the arrangement thereof in the immediate vicinity of the microelectrodes present in the carrier plate permits derivation of the electrical signals of the individual neurons.

FIGS. 2a and 2b show the effect of ultrafiltrates of a healthy experimentee (HEALTHY #1) and a patient (PATIENT #4) with severe liver failure prior to, during and after a specific therapy using the MARS procedure (Molecular Adsorbents Re-circulating System) for removal from the organism of toxic substances accumulating in the liver failure. Besides water-soluble metabolites they also involve relatively lipophilic substances. The latter are transported in the blood bound primarily to plasma proteins—in particular albumin. By virtue of the presence of acceptor proteins (albumin) in the dialyzate MARS permits the elimination of those otherwise scarcely dialyzable compounds from the blood plasma. In addition, that also provides for a favorable influence on the amino acid dysbalance between branched-chain and aromatic amino acids in the plasma, which is otherwise typical with that syndrome.

FIG. 2a shows the dependency of the burst rate (bursts per unit of time) and FIG. 2b shows the dependency of the spike rate (spikes per unit of time) on the addition of different ultrafiltrates. In that respect a spike represents the recorded activity of a neuronal action potential. The term burst is used to denote the very rapid succession of many action potentials in a neuronal unit over a closely restricted period of time in the form of "spike packets". The different activity configurations shown in the diagrams were each recorded by seven different extracellular electrodes of a multielectrode array during the same experiment. While scarcely any change in the activity of the cell assembly was found in the addition of the sample from the healthy person, after the addition of a sample, prepared in an identical manner, from a patient with severe liver failure with a hepatic coma of high degree, the situation involved a marked rise in the activity of a plurality of neuronal units while others remained relatively unaffected and in part even exhibited an inhibition in neuronal activity. The identically prepared samples from the same patient after the end of the first MARS treatment and after termination of the treatment series (5 individual treatments, one respective treatment per day) caused minor changes in the network activity in relation to the condition prior to the beginning of the experiment. In that respect a correlation with the duration of the MARS treatment effected and with the clinically detected degree of coma of the patient was revealed in such a way that the triggered changes also decreased with increasing treatment duration and decreasing degree of encephalopathy of the patients. Interim washing operations (partial change of the medium) showed the reversibility of the effects observed.

FIG. 3 shows a similar test procedure as shown in FIG. 2, with repetition of the test sequence, but on the basis of a different but similar cell assembly and using samples from another patient (PATIENT #1) who was also in a hepatic coma and was also treated in the same manner using the MARS process. In that respect, a high degree of reproducibility of the neuronal activity changes occurring after the addition of the various samples was found to occur.

The change in the activity of 13 neuronal units, shown by the different graphs, is represented as the product of burst rate and mean duration of the bursts per unit of time (referred to in the Figure as the "on-duty time"). The effects of the samples used on the network activity substantially correspond to those described with reference to FIG. 2. A slight change in activity is observed after addition of the sample from a healthy individual (HEALTHY #1) in comparison with initial activity of the network, but in contrast a high degree of activity in respect of the majority of the detected neuronal units after the addition of the sample from the patient (PATIENT #1) prior to the beginning of the MARS treatment. With an increasing duration of the MARS treatment, there is a progressively increasing reduction in the triggered changes and thus an approach to the effect of samples from the healthy person. In this case also a correlation of the extent of the caused effect of the samples on the neuronal activity with the clinically conspicuous degree of encephalopathy of the patient manifested itself. By repeating the sample sequence it was possible to demonstrate a high degree of reproducibility of the changes in neuronal activity occurring after the addition of the various samples.

FIG. 4 shows the comparison of the effects of ultrafiltrates of the blood plasma from four different patients (PATIENT #1-#4) with liver failure with higher-degree hepatic encephalopathy and a healthy individual (HEALTHY #1, tested at the beginning and at the end of the experiment) on the burst rate of six different units of a neuronal network. The change in network activity after the addition of the patient samples exhibited individual differences which point to a different substance composition of the ultrafiltrates. In that respect the difference in relation to the sample from the healthy individual was more or less pronounced. That can be a basis for a distinction in terms of various degrees of severity of the illness and the presence or absence of accompanying illnesses which are relevant in terms of the production of a coma. In regard to the burst rate, the splitting-up, occurring after the addition of the samples from patients to varying degrees, of the activity states of the individual neuronal units, illustrated in the Figure by the spacings of the graphs from each other, is the most pronounced feature (see also FIG. 2a) in comparison with samples from healthy individuals.

What is claimed is:

1. A method of extracorporeal detection of neurotoxic substances in the blood plasma of an individual comprising contacting neurons with a processed sample of the plasma and measuring electrical activity of the neurons, wherein the blood plasma of the individual is processed by subjecting it to an operation for the extraction of fat-soluble substances using a solvent for such fat-soluble substances to obtain an extracted fat soluble phase.

2. The method of claim 1 wherein the blood plasma is also subjected to a filtration process which provides for a very substantial separation of plasma proteins from other dissolved substances based upon molecular weight before extraction.

3. A method as set forth in claim 2 wherein the filtration process is carried out with an exclusion limit for the molecular weight of at most 45,000 Daltons.

4. A method as set forth in claim 2 wherein the filtration process is carried out with an exclusion limit for the molecular weight of at most 30,000 Daltons.

5. A method as set forth in claim 2 wherein dichloromethane or chloroform is used for the extraction of fat-soluble substances.

6. A method as set forth in claim 1 wherein the blood plasma is acidified prior to the extraction operation.

7. The method of claim 6 wherein the blood plasma is acidified using hydrochloric acid.

8. A method as set forth in claim 1 wherein the blood plasma is acidified prior to the extraction operation using an inorganic acid.

9. A method as set forth in claim 1 wherein dichloromethane or chloroform is used for the extraction of fat-soluble substances.

10. A method as set forth in claim 1 wherein after the extraction operation, the extracted fat soluble phase is transferred into a separate vessel, solvent with dissolved fat-soluble substances is removed by evaporation, and remaining extracted fat-soluble substances are re-dissolved by the addition of a suitable medium.

11. The method of claim 10 wherein the medium is a mixture of cell culture medium and a low concentration of an intermediary solvent.

12. The method of claim 11 wherein the intermediary solvent is dimethyl sulfoxide.

13. The method of claim 1 wherein the measuring electrical activity of the neurons is accomplished by the use of a system with neurons or neuronal networks applied or cultivated on a microelectrode array and a device for measuring the electrical activity of at least one or more of the neurons, for extracorporeal detection of neurotoxic substances in blood plasma of an individual, which neurotoxic substances will cause metabolic encephalopathies.

14. The method of claim 13 wherein the metabolic encephalopathy is hepatic encephalopathy.

15. A method as set forth in claim 13 for the differentiation of possible causes of disturbance of consciousness in unclear coma states.

16. The method of claim 1 wherein electrical activity of neurons is measured using a microelectrode array.

17. The method of claim 1 wherein the detection of neurotoxic substances is qualitative.

18. The method of claim 1 wherein the detection of neurotoxic substances is quantitative.

* * * * *